(12) United States Patent
Roh et al.

(10) Patent No.: US 8,766,135 B2
(45) Date of Patent: Jul. 1, 2014

(54) GLASS SUBSTRATE LASER CUTTING DEVICE WITH REAL-TIME BREAKING DETECTING FUNCTION AND GLASS SUBSTRATE BREAKAGE DETECTING METHOD THEREOF

(75) Inventors: Hyung-sang Roh, Incheon (KR); Ja-Yong Koo, Asan-si (KR); Sung Cheal Kim, Asan-si (KR); Won-Kyu Park, Cheonan-si (KR); Chang-Ha Lee, Asan-si (KR)

(73) Assignee: Samsung Corning Precision Materials Co., Ltd., Gum-Si (KR)

( * ) Notice: Subject to any disclaimer, the term of this patent is extended or adjusted under 35 U.S.C. 154(b) by 122 days.

(21) Appl. No.: 13/543,497

(22) Filed: Jul. 6, 2012

(65) Prior Publication Data

US 2013/0291593 A1 Nov. 7, 2013

(30) Foreign Application Priority Data

May 4, 2012 (KR) ........................ 10-2012-0047395

(51) Int. Cl.
| | |
|---|---|
| C03B 33/02 | (2006.01) |
| C03B 33/03 | (2006.01) |
| C03B 33/037 | (2006.01) |
| B23K 26/38 | (2014.01) |
| C03B 33/10 | (2006.01) |

(52) U.S. Cl.
CPC ................ C03B 33/02 (2013.01); C03B 33/03 (2013.01); C03B 33/037 (2013.01); C03B 33/102 (2013.01); B23K 26/38 (2013.01)
USPC ............ 219/121.62; 219/121.68; 219/121.69; 219/121.76; 219/121.83; 65/29.12; 65/29.18

(58) Field of Classification Search
CPC ...... C03B 33/02; C03B 33/03; C03B 33/037; C03B 33/102; B23K 26/38
USPC .............. 65/29.12, 29.18, 97, 105, 112, 166, 65/174; 219/121.62, 121.68, 121.69, 219/121.76, 121.83; 356/239.1–239.8; 250/559.43; 83/879, 880; 225/2, 96; 340/500

See application file for complete search history.

(56) References Cited

U.S. PATENT DOCUMENTS 4,054,867 A * 10/1977 Owens ........................... 340/550
5,191,218 A * 3/1993 Mori et al. ................ 250/453.11
(Continued)

FOREIGN PATENT DOCUMENTS

| KR | 10-2000-0054977 A | 9/2000 |
| KR | 10-2004-0036986 | 5/2004 |
| KR | 10-2006-0000623 A | 6/2006 |

(Continued)

OTHER PUBLICATIONS

Korean Office Action mailed Nov. 28, 2013, issued in corresponding Korean Patent Application No. 10-2012-0047395.

*Primary Examiner* — Samuel M Heinrich
(74) *Attorney, Agent, or Firm* — Stein IP, LLC

(57) ABSTRACT

A glass substrate laser cutting device according to the invention includes: a working table that has a plurality of vacuum absorbing grooves; a laser cutter; a pressure sensor that measures a pressure sensor when suctioning the glass substrate in a vacuum state; a calculation processing unit that compares the vacuum pressure measured by the pressure sensor with a predetermined threshold pressure and determines whether the glass substrate is broken; a laser cutter that includes a leaser head moving along the cutting direction of the glass substrate and emitting a laser beam; and an optical sensor that is attached to the laser head so as to move together and is disposed at a point in front of the laser beam emitted to the outside so as to detect the breakage of the glass substrate.

10 Claims, 7 Drawing Sheets

(56) References Cited

U.S. PATENT DOCUMENTS

| | | | |
|---|---|---|---|
| 5,689,332 A * | 11/1997 | Ellingson et al. | 356/237.1 |
| 6,723,952 B2 * | 4/2004 | Choo et al. | 219/121.72 |
| 7,866,185 B2 * | 1/2011 | Adriaansen et al. | 65/158 |
| 2006/0232403 A1 * | 10/2006 | Dang et al. | 340/550 |
| 2009/0014425 A1 * | 1/2009 | Zuehlke et al. | 219/121.72 |

FOREIGN PATENT DOCUMENTS

| | | |
|---|---|---|
| KR | 10-2009-0068945 A | 6/2009 |
| KR | 10-1066481 B1 | 9/2011 |

* cited by examiner

GLASS SUBSTRATE LASER CUTTING DEVICE WITH REAL-TIME BREAKING DETECTING FUNCTION AND GLASS SUBSTRATE BREAKAGE DETECTING METHOD THEREOF

CROSS-REFERENCE TO RELATED APPLICATIONS

This application claims the benefit of Korean Patent Application No. 10-2012-0047395, filed on May 4, 2012, in the Korean Intellectual Property Office, the disclosure of which is incorporated herein by reference.

BACKGROUND OF THE INVENTION

1. Field of the Invention

The present invention relates to a glass substrate laser cutting device and a glass substrate breakage detecting method, and more particularly, relates to a glass substrate laser cutting device with a real-time breakage detecting function capable of monitoring breakage of a glass substrate in real-time during a glass substrate cutting process by organically using a vacuum suction pressure and a laser cutter for cutting the glass substrate.

2. Description of the Related Art

In a process of cutting a glass substrate using a laser beam, it is very important to maintain flatness of a glass substrate which is a workpiece due to the nature of the process. Accordingly, the glass substrate generally cut by a laser is placed on a table which is highly precisely processed so as to have high flatness. As the material of the working table, metal, marble, or the like is widely used, and a sheet or a pad formed of a soft material is attached onto the working table so as to prevent damage of the surface of the glass substrate. However, since the sheet or the pad is formed of a combustible material, soot may be generated during combustion when the surface is irradiated with the laser beam, so that the optical system and the optical path are contaminated, which causes critical damage in the laser cutting device. Accordingly, since the combustible material of the sheet or the pad is exposed to a section in which the glass substrate is damaged, it is essential and important to determine whether the glass substrate as the workpiece is abnormal prior to the laser cutting.

As disclosed in Korean Patent No. 0510720, the existing glass substrate breakage detecting method is generally configured such that optical sensors are installed and fixed to both side surfaces of a glass substrate based on a glass substrate conveying direction and breakage of both side surfaces is detected when conveying the glass substrate.

In the above-described case, since the laser cutting direction is aligned with the glass substrate conveying direction, the optical sensors positioned at the lower or upper portions of both sides of the glass substrate may inspect the breakage state of both sides to be cut by a laser while the glass substrate is conveyed without a separate carriage.

Accordingly, in order to cut the other both side surfaces of the square glass substrate by a laser, there is a need to check whether the other both side surfaces are abnormal in the same manner as above. For this check, a device for changing the direction of the glass substrate needs to be provided. As a result, it is possible to determine whether all sides of the glass substrate are abnormal through all the above-described procedures.

However, in many cases, there is a limitation in that the damage of the laser optical system and the optical path caused by the damage of the glass substrate may not be basically prevented only by the existing glass substrate breakage detecting method.

That is, even when the glass substrate state of both sides to be cut by a laser is normal based on a time point at which the glass substrate is conveyed, if the breakage portions of the other both sides which are not detected upon aligning the glass substrate for the laser cutting process increase in size and the combustible material below the glass substrate is exposed, there is a problem in that soot generated during the laser cutting contaminates the optical system and the optical path.

SUMMARY OF THE INVENTION

The present invention is directed to providing a glass substrate laser cutting device with a real-time breakage detecting function capable of inspecting breakage of a glass substrate caused by abnormality of both sides other than both sides of the glass substrate subjected to laser cutting and particularly detecting damage of the glass substrate in all cases and occurring in a series of procedures of a laser cutting process by detecting whether the glass substrate is broken in real-time not only when conveying the glass substrate but also right before and while cutting the glass substrate by a laser when advancing to the laser cutting process, and a glass substrate breakage detecting method thereof.

In order to attain the above-described object, there is provided a glass substrate laser cutting device with a real-time breakage detecting function including: a working table that has a plurality of vacuum absorbing grooves suctioning a glass substrate in a vacuum state; a laser cutter that cuts the glass substrate suctioned to the working table in a vacuum state by allowing the glass substrate to be irradiated with a laser beam; a pressure sensor that measures a vacuum pressure when the working table suctions the glass substrate in a vacuum state; a calculation processing unit that determines whether the glass substrate is broken through a calculation of comparing the vacuum pressure measured by the pressure sensor with a predetermined threshold pressure; a laser cutter that includes a laser head moving along the cutting direction of the glass substrate and emitting the laser beam to the glass substrate; and an optical sensor that is attached to the laser head so as to move together and is disposed at a point in front of at least the laser beam emitted to the outside based on the cutting direction of the glass substrate so as to detect the breakage of the glass substrate.

In order to attain the above-described object, there is provided a glass substrate breakage detecting method including the steps of: fixing the glass substrate onto the top surface of the working table through vacuum suction; measuring a vacuum pressure when the working table suctions the glass substrate in a vacuum state; comparing the measured vacuum pressure with a predetermined threshold pressure and determining whether the glass substrate is broken on the basis of the comparison result; and advancing to a glass substrate cutting process when the glass substrate is normal as the determination result and delaying the glass substrate cutting process when the glass substrate is abnormal as the determination result so as to display the abnormal state to the outside.

According to the glass substrate laser cutting device with the real-time breakage detecting function and the glass substrate breakage detecting method thereof in accordance with the invention, since it is possible to monitor the damage of the glass substrate in all cases and occurring in all procedures of the laser cutting process not only when conveying the glass substrate but also when performing the glass substrate cutting process, it is possible to previously prevent critical damage from occurring due to contamination of an optical system and an optical path of the laser cutting process in the case where the damage is not detected. Accordingly, there is an excellent advantage in that not only the performance in the yield rate of the laser cutting system but also the safety in the operation may be remarkably improved.

Furthermore, since the breakage of the glass substrate may be detected in real-time by directly using the vacuum suction pressure essentially necessary for cutting the glass substrate, it is possible to manufacture the glass substrate laser cutting device very economically without an increase in cost. Accordingly, there is an advantage in that the industrial applicability is high.

Furthermore, since the vacuum absorbing grooves detecting the breakage of the glass while realizing the vacuum suction of the glass substrate are densely formed in a lattice shape, a change in the vacuum pressure easily occurs even when breakage is present on any point of the glass substrate suctioned and fixed to the working bar or the breakage is minute. Accordingly, there is a noticeable advantage in that the performance and the accuracy of detecting the breakage of the glass substrate may be further improved.

Additional aspects and/or advantages of the invention will be set forth in part in the description which follows and, in part, will be obvious from the description, or may be learned by practice of the invention.

BRIEF DESCRIPTION OF THE DRAWINGS

These and/or other aspects and advantages of the invention will be apparent and more readily appreciated from the following description of the embodiments, taken in conjunction with the accompanying drawings in which.

DETAILED DESCRIPTION OF THE EMBODIMENTS

Figure 1:
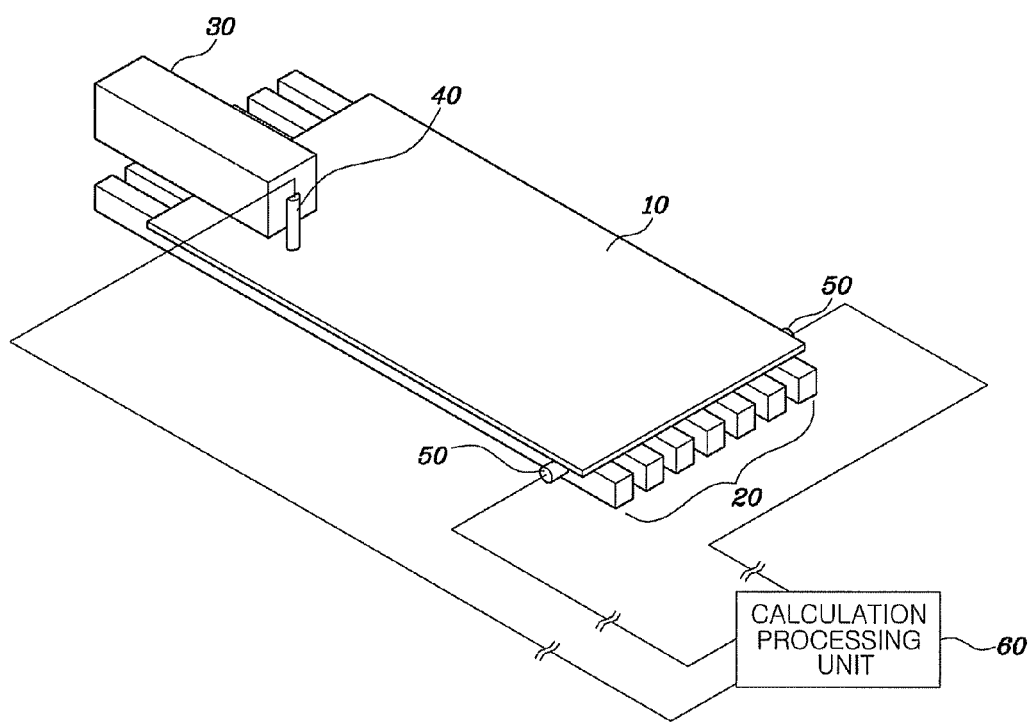
FIG. 1 is a diagram schematically showing a configuration of a glass substrate laser cutting device with a real-time breakage detecting function according to the invention.

Reference will now be made in detail to the present embodiments of the present invention, examples of which are illustrated in the accompanying drawings, wherein like reference numerals refer to the like elements throughout. The embodiments are described below in order to explain the present invention by referring to the figures.

The invention discloses a technology capable of monitoring breakage of a glass substrate in real-time during a process of cutting the glass substrate by organically using a vacuum suction pressure for fixing the glass substrate and a laser cutter for cutting the glass substrate.

Hereinafter, preferred embodiments, advantages, and features of the invention will be described in detail by referring to the accompanying drawings.

Prior to description, the term of a 'real-time glass substrate breakage detecting function' used in the invention indicates a function of immediately detecting occurrence of breakage from a time point right before cutting a glass substrate using a laser to a time point after completing the laser cutting through a time point at which the glass substrate is being cut by a laser and carrying out a process appropriate for the situation, other than the existing glass substrate breakage detecting process performed separately from the glass substrate cutting process.

FIG. 1 is a diagram schematically showing a glass substrate laser cutting device with a real-time breakage detecting function according to the invention.

Referring to FIG. 1, the glass substrate laser cutting device with the real-time breakage detecting function of the invention includes a working table 20, a laser cutter 30, a pressure sensor 50, a calculation processing unit 60, an optical sensor 40, and a control unit.

The working table 20 corresponds to a component that supports, conveys, and fixes a glass substrate 10.

When cutting the glass substrate 10 by a laser, it is very important to maintain the flatness of the glass substrate as a workpiece to be constant due to the nature of the process. Accordingly, the working table 20 is processed with high precision so as to have high flatness and is formed of metal or marble for the highly precise process.

Furthermore, the glass substrate 10 is loaded on the top surface of the working table 20 so as to be supported, transported, and fixed thereto. At this time, a sheet or a pad formed of a soft material is attached to the top surface of the working table 20 in order to prevent surface damage of the glass substrate 10.

On the other hand, the working table 20 is provided with gas flow holes 24 and 27 and an air pipe which are used to convey or fix the glass substrate 10. A plurality of gas flow holes 24 and 27 are formed in the top surface of the working table on which the glass substrate 10 is loaded, and the air pipe is used as a passageway, into and from which a gas is injected and discharged, and communicates with each of the gas flow holes 24 and 27.

Furthermore, the air pipe is connected to a nozzle 26 so that a gas is injected thereinto so as to convey the glass substrate 10 and a gas is discharged therefrom so as to fix the glass substrate 10, and the nozzle 26 is connected to an air pressure unit or a vacuum pump 70 so as to realize a positive (+) pressure through the gas injection and a vacuum pressure through the gas discharge.

If the operation of conveying the glass substrate 10 using the working table 20 is investigated, when a gas is injected from the nozzle 26 so as to apply a positive pressure into the working table, a thin air layer is formed between the glass substrate 10 and the working table, so that the glass substrate 10 is minutely lifted. At this time, the glass substrate is conveyed while sliding on the working table 20 without any surface damage in the state where a frictional force is minimized.

If the operation of fixing the glass substrate 10 using the working table 20 is investigated, when a vacuum pressure is applied into the working table through a pumping action, the glass substrate 10 is suctioned onto the working table 20 in a vacuum state, so that it is immovably fixed thereto.

In particular, the working table 20 of the invention includes at least three or more working bars 21, 22, and 23 arranged in parallel at an interval therebetween. The air pipes 25 of the working bars (hereinafter, referred to as "a left-side working bar 22 and a right-side working bar 21") positioned perpendicularly below the left side portion and the right side portion of the glass substrate 10 loaded on the working table in the plurality of working bars 21, 22, and 23 are separated from the air pipe of the other working bar 23. This will be described later in detail.

A laser cutter 30 corresponds to a component that is attached to the perpendicular upper portion of the working table 20, moves along a glass substrate cutting direction D1, and cuts the glass substrate 10 by allowing the glass substrate to be irradiated with a laser beam.

Specifically, the laser cutter 30 includes a heating device that generates a laser beam so as to rapidly heat the glass substrate 10 and a cooling device that rapidly cools the glass substrate 10 by spraying cooling water thereto so that a crack grows along a predetermined cutting line of the glass substrate 10.

The pressure sensor 50 indicates a vacuum pressure sensor that is installed to be connected to the inside of the working table (that is, a vacuum absorbing groove and an air pipe) and measures a vacuum degree when the working table 20 suctions the glass substrate 10 in a vacuum state.

In particular, the invention is characterized in that the working table 20 includes at least three or more separate working bars and the vacuum pressures of the left-side working bar 22 and the right-side working bar 21 in the plurality of working bars are measured. Accordingly, the pressure sensor 50 may be installed so as to be connected to the left-side working bar 22 and the right-side working bar 21 so as to simultaneously measure the vacuum degrees thereof or the separate pressure sensors 50 may be respectively connected to the left-side working bar 22 and the right-side working bar 21 so as to independently measure the vacuum degrees thereof.

On the other hand, the vacuum pressures of the left-side and right-side working bars 21 measured by the pressure sensor 50 are transmitted to the calculation processing unit 60 electrically connected to the pressure sensor 50, and is used as the basis for determining whether the glass substrate 10 is broken. The determination method will be described later in detail.

The optical sensor 40 corresponds to a component that moves along with the laser cutter 30 in order to cut the glass substrate and detects the breakage of the glass substrate while the laser cutting is performed. The embodiment of FIG. 1 is configured such that the optical sensor 40 is attached to the laser cutter 30 so as to be movable along with the laser cutter 30.

The optical sensor 40 may be configured as a photo sensor including a light emitting portion emitting light and a light receiving portion receiving emitted light or a laser sensor. The light emitting portion is provided at one side of the optical sensor 40 and the light receiving portion is provided at the other side thereof, so that the damage or the scratch of the glass substrate may be detected by the combination of the light emitting portion and the light receiving portion.

On the other hand, sensing information measured by the optical sensor 40 is transmitted to the calculation processing unit 60 electrically connected to the optical sensor 40 and is used as the basis for determining whether the glass substrate is damaged. The determination method will be described later in detail.

The control unit is electrically connected to a laser cutter driving unit (not shown) controlling the driving of the laser cutter 30, and realizes a function of immediately stopping the irradiation of the laser beam by controlling the laser cutter driving unit when the damage of the glass substrate is detected through the optical sensor 40.

Figure 2:
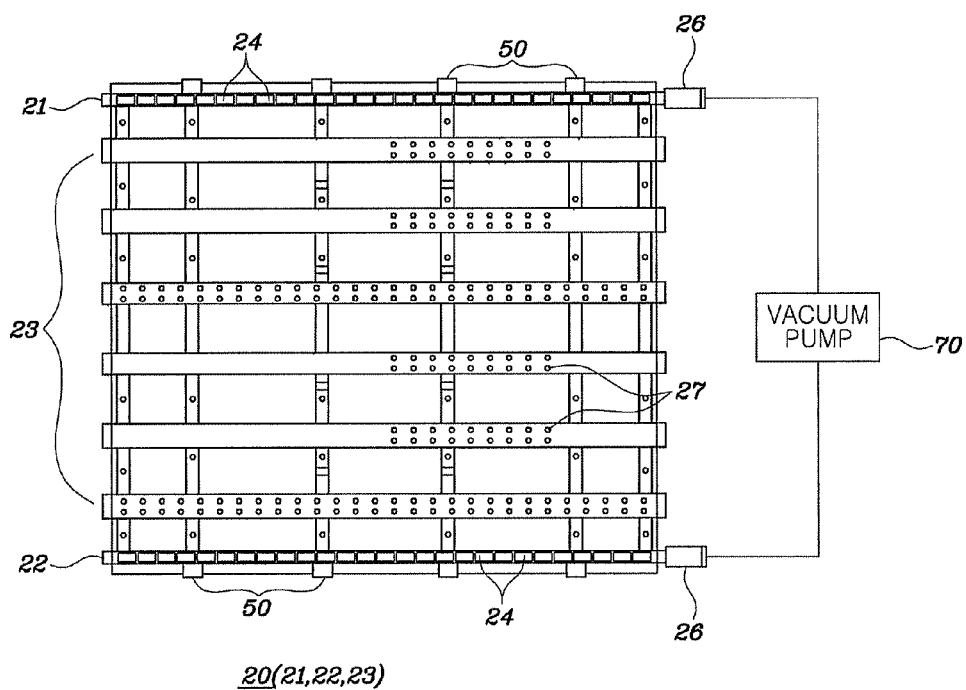
FIG. 2 is a plan view of a working table according to a preferred embodiment of the invention.
Figure 3:
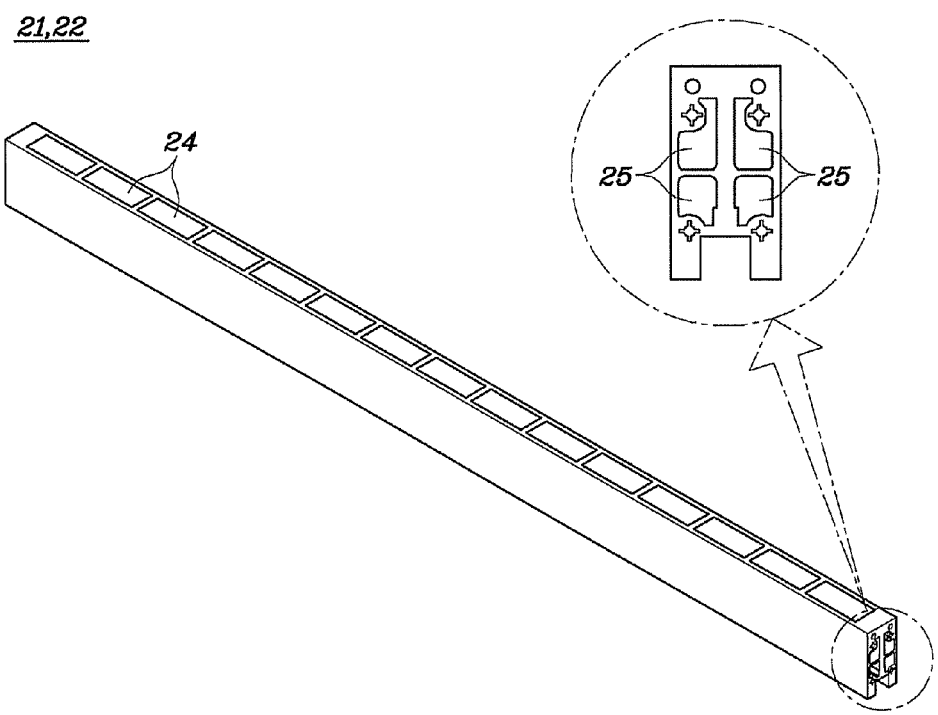
FIG. 3 is a perspective view of left-side and right-side working bars according to the preferred embodiment of the invention.

FIG. 2 is a plan view of the working table according to the preferred embodiment of the invention, and FIG. 3 is a perspective view of the left-side and right-side working bars according to the preferred embodiment of the invention.

Referring to FIGS. 2 and 3, the working table 20 according to the preferred embodiment of the invention includes a plurality of working bars formed in a beam shape with an elongated shaft linear in one direction, and the plurality of working bars are arranged in parallel to the glass substrate cutting direction D1 at an interval therebetween.

In the plurality of working bars, the air pipes of the left-side working bar 22 and the right-side working bar 21 positioned at the perpendicular lower portions of the left side portion and the right side portion of the glass substrate loaded on the working table 20 are separated from the air pipe of the other working bar 23.

The upper portions of the left-side working bar 22 and the right-side working bar 21 are provided with a plurality of vacuum absorbing grooves 24 formed in the longitudinal direction thereof so as to fix the glass substrate through a vacuum suctioning operation, and the inner portions of the left-side working bar 22 and the right-side working bar 21 are provided with the air pipes 25 connected to the vacuum absorbing grooves 24 so as to communicate therewith.

As shown in FIG. 3, it is desirable that the vacuum absorbing grooves 24 formed in the left-side working bar 22 and the right-side working bar 21 be formed in a dense lattice shape in the top surface of the left-side working bar (or the right-side working bar) along the longitudinal direction of the beam.

This is because it is advantageous to guarantee high accuracy of performance of detecting the damage of the glass substrate by easily causing a change in the vacuum pressure using the vacuum absorbing grooves 24 densely provided in the lattice shape even when damage occurs in a certain point of the glass substrate suctioned and fixed to the top surfaces of the left-side working bar 22 and the right-side working bar 21 or the damage is slight.

On the other hand, the terminal ends of the air pipes 25 of the left-side working bar 22 and the right-side working bar 21 are connected to the vacuum pump 70 through the nozzles 26, so that the vacuum suction operation may be performed through the pumping action of the vacuum pump 70.

Furthermore, all vacuum absorbing grooves 24 formed in the left-side working bar or the right-side working bar are organically connected to each other through the air pipes 25. Accordingly, even when damage occurs at an arbitrary position of the left side or the right side of the glass substrate to be subjected to laser cutting, there is a difference in the vacuum pressure compared to the case of the normal glass substrate, so that the abnormal state of the glass substrate may be detected.

The upper portion of the other working bar 23 except for the left-side working bar 22 and the right-side working bar 21 is provided with a plurality of air lift grooves 27 which are provided in the longitudinal direction and lift the glass substrate using air so as to convey the glass substrate, and the inner portion thereof is provided with an air pipe connected to the air lift grooves 27 so as to communicate with each other.

On the other hand, the air pipe formed in the other working bar 23 may be connected to the vacuum pump 70 together with the air pipes 25 of the left-side working bar 22 and the right-side working bar 21 or may be connected to a separate air pressure unit.

For reference, it is illustrated and shown as above such that the left-side working bar 22 and the right-side working bar 21 fix the glass substrate and the other working bar 23 conveys the glass substrate. However, all the left-side working bar 22, the right-side working bar 21, and the other working bar 23 may be, of course, connected to one vacuum pump or one air pressure unit, so that the vacuum absorbing grooves 24 and the air lift grooves 27 perform substantially the same function (that is, a function of conveying the glass substrate by a gas injecting operation and suctioning the glass substrate in a vacuum state by a gas pumping operation).

Figure 4:
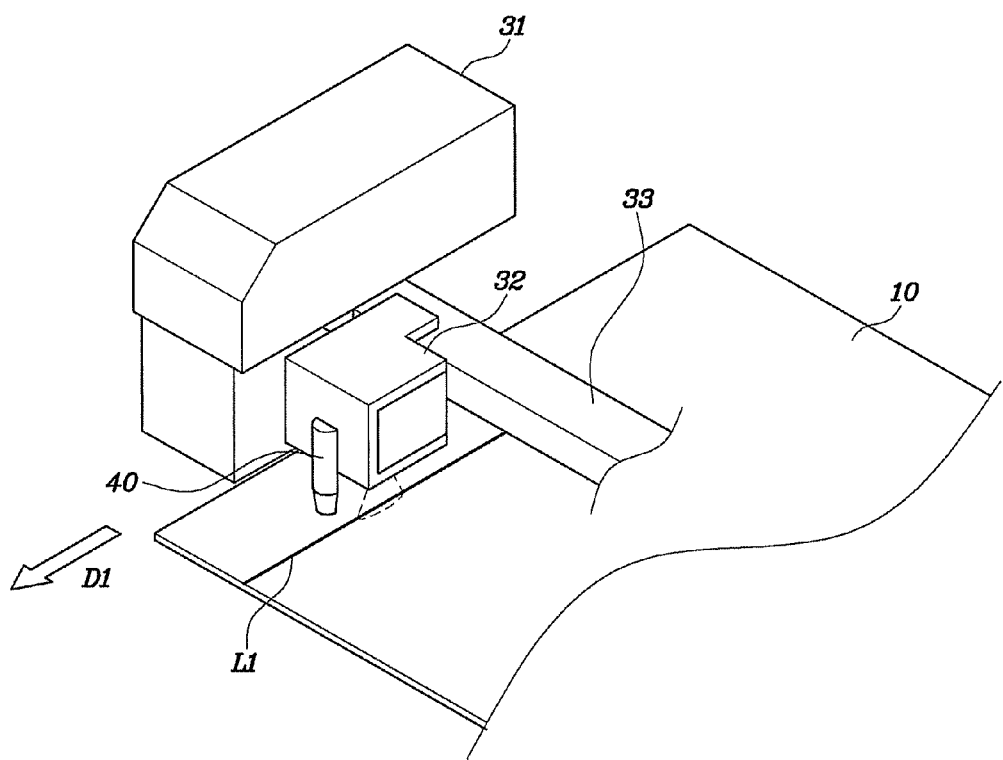
FIG. 4 is a schematic diagram of a laser cutter equipped with an optical sensor according to the preferred embodiment of the invention.
Figure 5:
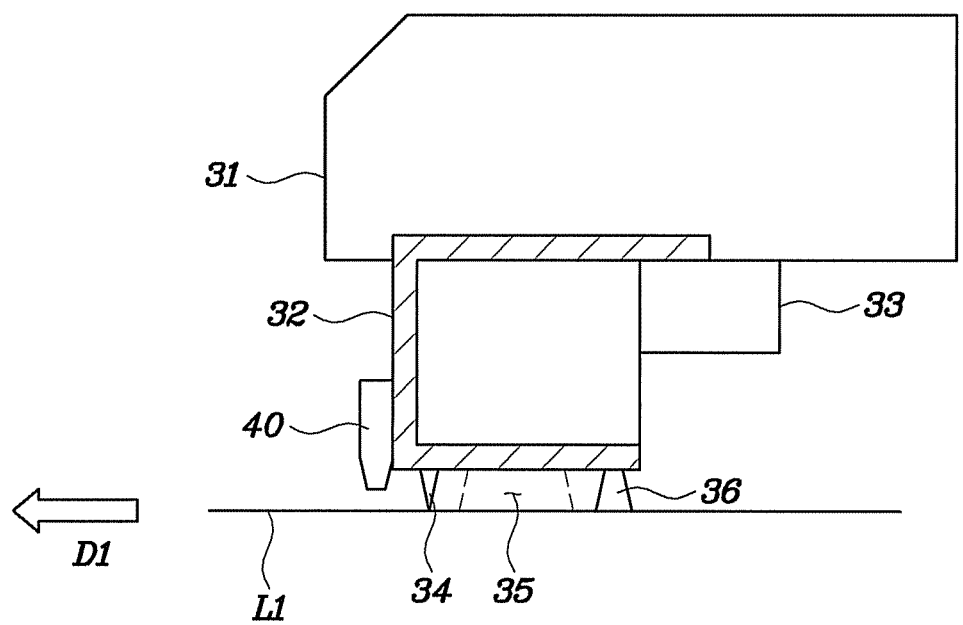
FIG. 5 is a side view of FIG. 4.

FIG. 4 is a schematic diagram of the laser cutter with the optical sensor according to the preferred embodiment of the invention, and FIG. 5 is a side view of FIG. 4.

Referring to FIGS. 4 and 5, the laser cutter 30 according to the preferred embodiment of the invention includes a heating device and a cooling device, and an optical sensor 40 is attached to one side of the laser cutter.

The heating device includes a laser source 31 that generates a hot laser beam 35, a laser head 32 that emits a laser beam generated from the laser source 31 to the glass substrate 10, and a gantry beam 33 that supports the laser head 32 so that it is movable on the perpendicular upper portion of the glass substrate 10, and may desirably further include a refraction lens unit that refracts the scanning direction of the laser beam generated from the laser source 31 and a focusing lens unit that adjusts a focus of the refracted laser beam.

Furthermore, the laser head 32 may further include an initial crack generating unit 34 that generates an initial crack on the surface of the glass substrate 10 before the cutting using the laser beam.

The cooling device includes an ejection nozzle 36 that is installed at a point in rear of the laser emitted to the outside based on the direction (that is, the glass substrate cutting direction D1) in which a crack advances and sprays cooling water to the heated glass substrate 10, and may desirably further include a cooling water storage tank that supplies a cooling fluid toward the ejection nozzle 36.

The optical sensor 40 of the embodiment of FIGS. 4 and 5 is attached to the later head 32 and moves along with the laser cutter 30 cutting the glass substrate 10 so as to monitor whether a breakage portion is present on a predetermined cutting line in real-time.

More specifically, the optical sensor 40 is disposed and fixed to one point of the laser head 32, where the one point indicates a point in front of the laser beam 35 emitted to the outside from at least the laser head 32 based on the glass substrate cutting direction D1, and more desirably, a point having a sensing area disposed on the line L1 which is the same at least the axis of the laser beam emitted to the glass substrate 10 in the front point.

This is because the laser beam needs to be interrupted before it reaches a breakage portion when the breakage portion of the glass substrate 10 is detected in real-time during the laser cutting. Accordingly, it is possible to prevent an optical system and an optical path from being contaminated due to the combustion of the working table. Accordingly, in order to attain the above-described object, the optical sensor 40 is disposed at a position in front of the laser beam and inspects a predetermined cutting portion in advance. When any abnormality is not detected as an inspection result, the corresponding portion may be cut by the laser beam.

That is, the pre-inspection process using the optical sensor 40 and the post-cutting process using the laser beam are continuously performed for each point of the predetermined cutting line of the glass substrate, thereby basically preventing the optical system and the optical path from being contaminated by the breakage portion occurring during the laser cutting.

On the other hand, when the breakage of the glass substrate 10 is detected by the optical sensor 40, the control performs an operation of preventing the working table from being burned by the breakage portion by immediately stopping the irradiation of the laser beam 35 of the laser cutter 30.

Accordingly, the optical sensor 40 is installed at a position in front of the laser beam, and the distance between the optical sensor 40 and the front end of the laser beam is determined in consideration of a time until the laser beam becomes an off state after detecting the breakage of the glass substrate using the optical sensor 40. More specifically, the distance is calculated in consideration of the laser cutting speed and the time spent for the communication regarding the generation of laser from the optical sensor 40 so as to ensure a distance capable of ensuring a delay time spent for preventing the laser beam from reaching a breakage portion after detecting the breakage portion using the optical sensor 40.

Figure 6:
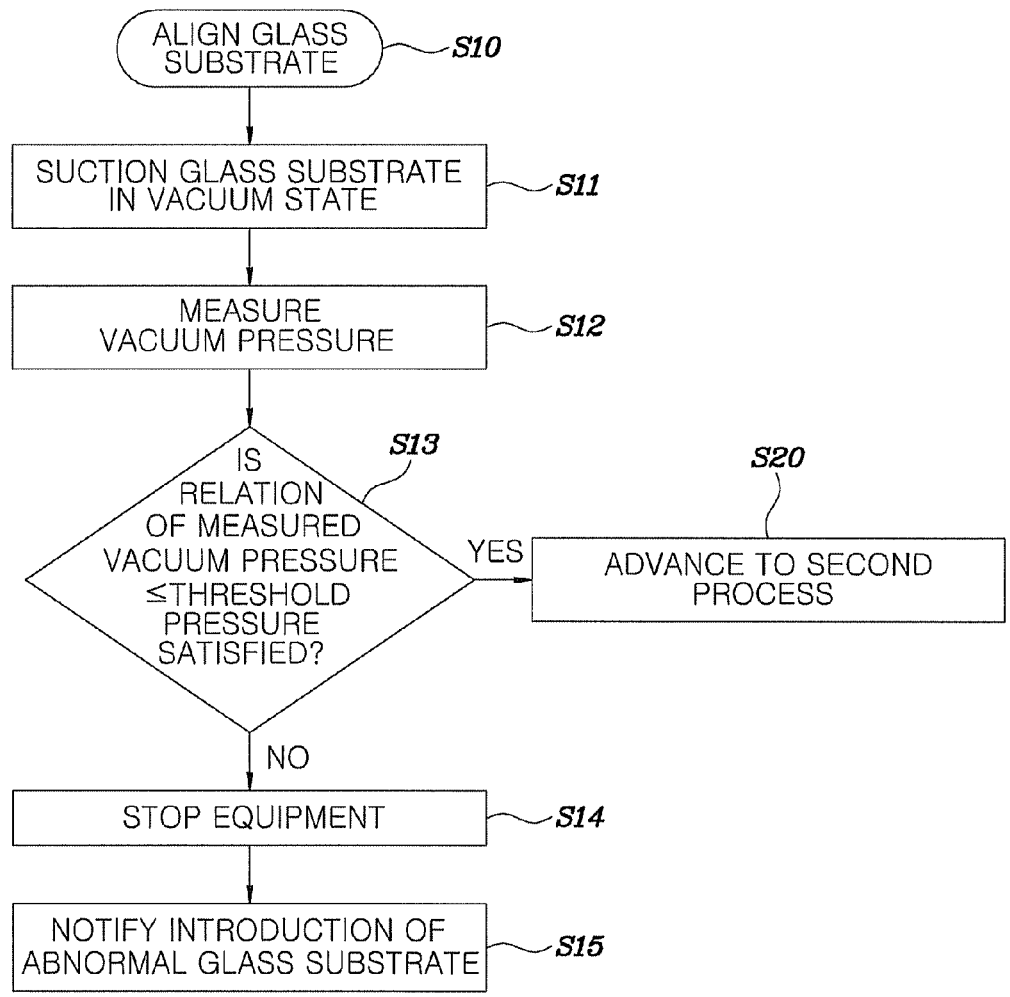
FIG. 6 is a flowchart showing a process sequence of a first process of inspecting whether a glass substrate is broken right before the start of cutting in a glass substrate cutting process using a glass substrate laser cutting device according to the invention.
Figure 7:
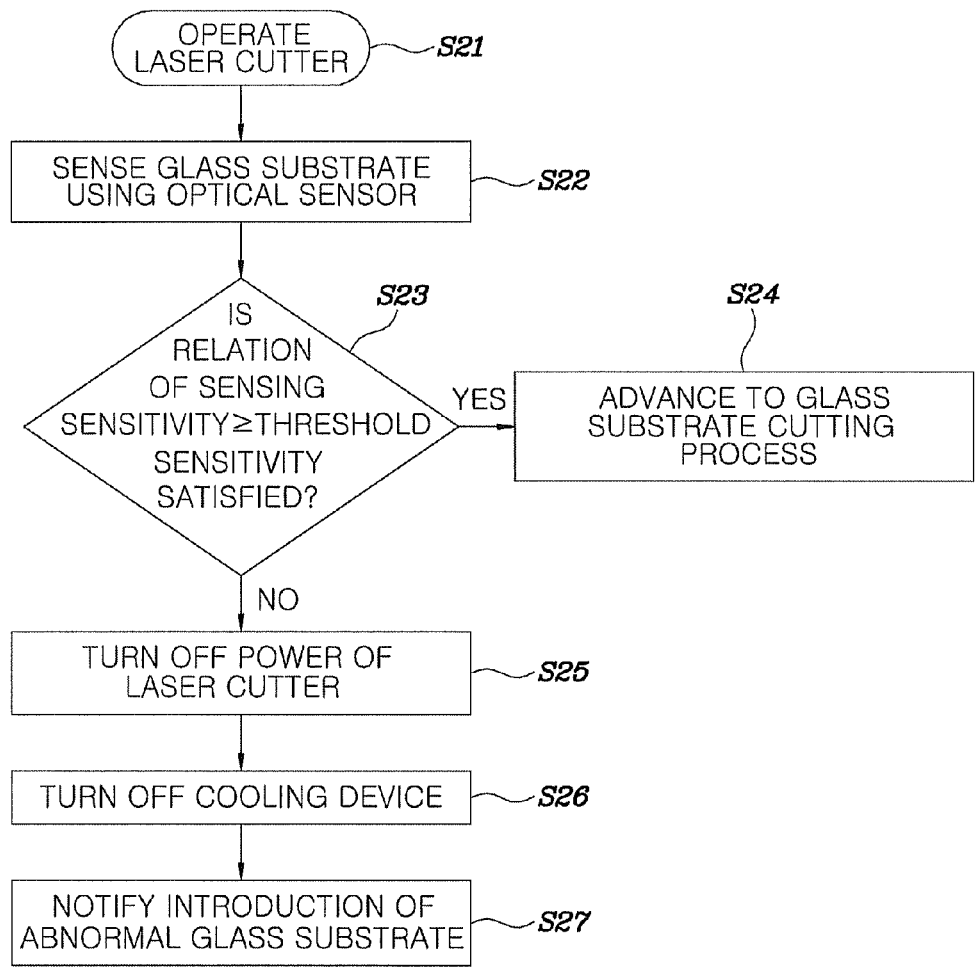
FIG. 7 is a block flowchart showing a process sequence of a second process of inspecting whether a glass substrate is broken while performing laser cutting in the glass substrate cutting process using the glass substrate laser cutting device according to the invention.

FIGS. 6 and 7 are block flowcharts showing a sequence of detecting and handling occurrence of breakage in the glass substrate in real-time in the process of cutting the glass substrate using the glass substrate laser cutting device according to the invention, FIG. 6 is a block flowchart of a first process right before cutting the glass substrate, and FIG. 7 is a block flowchart of a second process while cutting the glass substrate.

The glass substrate cutting process using the glass substrate laser cutting device according to the invention includes the first process in which occurrence of breakage of the glass substrate is inspected right before cutting the glass substrate and the second process in which occurrence of breakage of the glass substrate is inspected while cutting the glass substrate.

Referring to FIG. 6, the first process includes a step (S10) of aligning the glass substrate loaded on the working table 20, a step (S11) of operating the vacuum pump 70 so as to apply a vacuum pressure to at least the left-side working bar 22 and the right-side working bar 21, so that the glass substrate is suctioned in a vacuum state, a step (S12) of measuring a vacuum pressure using the pressure sensor 50 when the working table 20 suctions the glass substrate in a vacuum state, and a step (S13) of comparing the vacuum pressure measured by the pressure sensor 50 with a threshold pressure.

The calculation of comparing the vacuum pressure measured by the pressure sensor 50 with the threshold pressure is performed by the calculation processing unit 60 electrically connected to the pressure sensor 50, and the numerical value for the threshold pressure is set and stored in advance in the calculation processing unit 60. Furthermore, the threshold pressure indicates the vacuum pressure numerical value which may be maximally allowed in the range of the vacuum pressure formed when the glass substrate is normally suctioned to the working table 20 in a vacuum state.

Accordingly, when the vacuum pressure measured by the pressure sensor 50 is equal to or, lower than the threshold pressure (hereinafter, a 'case 1'), it may be estimated that the glass substrate is normally suctioned in a vacuum state and hence no breakage portion is present on the glass substrate.

In contrast, when the vacuum pressure measured by the pressure sensor 50 is higher than the threshold pressure (hereinafter, a 'case 2'), it may be estimated that the glass substrate is not properly suctioned in a vacuum state and hence a breakage portion is present on a predetermined point of the left side portion or the right side portion of the glass substrate.

When the case 2 is determined as a comparison result between the vacuum pressure measured by the pressure sensor 50 and the threshold pressure, the operation of the glass substrate laser cutting device is stopped (S14), and the fact that the abnormal glass substrate is introduced is notified to an operator with time (or alarm sound) (S15).

When the case 1 is determined as a comparison result between the vacuum pressure measured by the pressure sensor 50 and the threshold pressure, the second process for laser cutting is performed (S20).

The second process includes a step (S21) of operating the laser cutter 30 so as to move along the predetermined cutting line, a step (S22: hereinafter, a 'sensing step') of moving the optical sensor 40 attached with the laser cutter 30 prior to the laser beam emitted from the laser cutter 30 so as to sense the glass substrate, a step (S23: hereinafter, a 'determination step') of comparing the sensing sensitivity sensed by the optical sensor 40 with a threshold sensitivity, and a step (S24: hereinafter, a 'cutting step') of cutting the glass substrate using a laser beam. On the other hand, the sensing step (S22), the determination step (S23), and the cutting step (S24) are continuously repeated at each point of the predetermined cutting line of the glass substrate.

The calculation of comparing the sensing sensitivity measured by the optical sensor 40 with the threshold sensitivity is performed by the calculation processing unit 60 electrically connected to the optical sensor 40, and the threshold sensitivity is set and stored in advance in the calculation processing unit 60. Furthermore, the threshold sensitivity indicates a value which may be minimally allowed in the range of the sensitivity measured in a manner such that the optical sensor 40 emits a beam to the surface of the normal glass substrate and receives the light reflected therefrom.

Accordingly, when the sensing sensitivity measured by the optical sensor 40 is equal to or larger than the threshold sensitivity (hereinafter, a 'case 3'), it may be estimated that no breakage portion is present near the predetermined cutting line of the glass substrate.

In contrast, when the sensing sensitivity measured by the optical sensor 40 is smaller than the threshold sensitivity (hereinafter, a 'case 4'), it may be estimated that a breakage portion is present near the predetermined cutting line of the glass substrate.

When the case 4 is determined as a comparison result between the sensing sensitivity measured by the optical sensor 40 and the threshold sensitivity, the power of the laser cutter 30 is turned off (S25) so as to stop the laser beam 35 which is being emitted and stop the cooling water which is being sprayed (S26). Then, the fact that the abnormal glass substrate is introduced is notified to the operator with time (or alarm sound) (S27).

When the case 3 is determined as a comparison result between the sensing sensitivity measured by the optical sensor 40 and the threshold sensitivity, the glass substrate cutting process using the laser beam is normally performed.

Subsequently, when the cutting of the glass substrate is completed, the glass substrate is unloaded and is moved and stored in a designated place, thereby ending the glass substrate breakage detecting and cutting process.

The preferred embodiment of the invention has been illustrated and shown using specific terms, but those terms are used only for clearly describing the invention. It is obvious that the embodiment and the technical terms of the invention may be variously modified and changed without being deviated from the technical spirit and the scope of claims below.

For example, the calculation processing unit 60 and the control unit are described and shown as separate components, but it is obvious by the person skilled in the art that those functions may be performed by one central processing unit. Furthermore, the calculation processing unit 60 is configured to perform a function of determining occurrence of breakage using a vacuum pressure and detecting breakage using sensing sensitivity by being interlocked with not only the optical sensor 40 but also the pressure sensor 50, but the calculation processing unit for the optical sensor 40 and the calculation processing unit for the pressure sensor 50 may be, of course, separately provided.

While the preferred embodiments have been shown and described, it will be understood by those skilled in the art that various changes in form and details may be made thereto without departing from the spirit and scope of this invention as defined by the appended claims.

In addition, many modifications can be made to adapt a particular situation or material to the teachings of this invention without departing from the essential scope thereof. Therefore, it is intended that this invention not be limited to the particular preferred embodiments disclosed as the best mode contemplated for carrying out this invention, but that this invention will include all embodiments falling within the scope of the appended claims.

What is claimed is:

1. A glass substrate laser cutting device with a real-time breakage detecting function comprising:
   a working table that has a plurality of vacuum absorbing grooves suctioning a glass substrate in a vacuum state;
   a laser cutter that cuts the glass substrate suctioned to the working table in a vacuum state by allowing the glass substrate to be irradiated with a laser beam;
   a pressure sensor that measures a vacuum pressure when the working table suctions the glass substrate in a vacuum state; and
   a calculation processing unit that determines whether the glass substrate is broken through a calculation of comparing the vacuum pressure measured by the pressure sensor with a predetermined threshold pressure.

2. The glass substrate laser cutting device with the real-time breakage detecting function according to claim 1, further comprising:
   a laser cutter that includes a laser head moving along the cutting direction of the glass substrate and emitting the laser beam to the glass substrate; and
   an optical sensor that is attached to the laser head so as to move together and is disposed at a point in front of at least the laser beam emitted to the outside based on the cutting direction of the glass substrate so as to detect the breakage of the glass substrate.

3. The glass substrate laser cutting device with the real-time breakage detecting function according to claim 2,
   wherein the optical sensor is disposed at a point having a sensing area positioned on a line L1 which is the same as at least the axis of the laser beam emitted to the glass substrate in the front point.

4. The glass substrate laser cutting device with the real-time breakage detecting function according to claim 2, further comprising:
   a calculation processing unit that determines whether the glass substrate is broken through a calculation of comparing sensing sensitivity measured by the optical sensor with a predetermined threshold value.

5. The glass substrate laser cutting device with the real-time breakage detecting function according to claim 4, further comprising:
- a control unit that stops the irradiation of the laser beam of the laser cutter when the breakage of the glass substrate is detected through the optical sensor.

6. The glass substrate laser cutting device with the real-time breakage detecting function according to claim 1,
- wherein the working table includes at least three or more working bars arranged in parallel at an interval therebetween,
- wherein the vacuum absorbing grooves are respectively formed in working bars (hereinafter, referred to as "left-side and right-side working bars") positioned at the perpendicular lower portions of a left side portion and a right side portion of the glass substrate loaded on the working table,
- wherein the left-side working bar and the right-side working bar are provided with air pipes realizing the vacuum suction and communicating with the vacuum absorbing grooves,
- wherein the air pipes of the left-side working bar and the right-side working bar are separated from an air pipe formed in the other working bar, and
- wherein the pressure sensor is configured to measure the vacuum pressures formed in the left-side working bar and the right-side working bar.

7. The glass substrate laser cutting device with the real-time breakage detecting function according to claim 6,
- wherein the left-side working bar and the right-side working bar are formed in a beam shape, and
- wherein the vacuum absorbing grooves of the left-side working bar and the right-side working bar communicate with each other and are formed in a lattice shape along the longitudinal direction of the beam.

8. The glass substrate laser cutting device with the real-time breakage detecting function according to claim 2,
- wherein the optical sensor is a photo sensor including a light emitting portion and a light receiving portion or a laser sensor.

9. A glass substrate breakage detecting method of a glass substrate laser cutting device with a real-time breakage detecting function, the glass substrate breakage detecting method being used to cut a glass substrate by a laser while monitoring occurrence of breakage of the glass substrate loaded on a working table in real-time, the glass substrate breakage detecting method comprising the steps of:
- fixing the glass substrate onto the top surface of the working table through vacuum suction;
- measuring a vacuum pressure when the working table suctions the glass substrate in a vacuum state;
- comparing the measured vacuum pressure with a predetermined threshold pressure and determining whether the glass substrate is broken on the basis of the comparison result; and
- advancing to a glass substrate cutting process when the glass substrate is normal as the determination result and delaying the glass substrate cutting process when the glass substrate is abnormal as the determination result so as to display the abnormal state to the outside.

10. The glass substrate breakage detecting method of the glass substrate laser cutting device with the real-time breakage detecting function according to claim 9, further comprising the steps of:
- causing the laser cutter to move along a predetermined cutting line when the glass substrate advances to the glass substrate cutting process;
- causing an optical sensor attached to the laser cutter to move prior to the front end of the laser beam emitted from the laser cutter and to sense the glass substrate;
- comparing sensing sensitivity sensed by the optical sensor with a predetermined threshold value and determining whether the glass substrate is broken on the basis of the comparison result; and
- normally performing the glass substrate cutting using the laser beam when the glass substrate is normal as the determination result and immediately stopping the irradiation of the laser beam of the laser cutter when the glass substrate is abnormal as the determination result.

* * * * *